United States Patent [19]

Meilland

[11] Patent Number: Plant 6,165

[45] Date of Patent: May 3, 1988

[54] ROSE PLANT—MEIROSPRAY VARIETY

[75] Inventor: Marie-Louise Meilland, Antibes, France

[73] Assignee: The Conrad-Pyle Company, West Grove, Pa.

[21] Appl. No.: 833,615

[22] Filed: Feb. 27, 1986

[51] Int. Cl.[4] ..... A01H 5/00

[52] U.S. Cl. ..... Plt./25

[58] Field of Search ..... Plt./25

*Primary Examiner*—Robert E. Bagwill

*Attorney, Agent, or Firm*—Burns, Doane, Swecker & Mathis

[57] ABSTRACT

A new and distinct variety of Floribunda rose plant is provided which simultaneously forms attractive multiple blossom floral sprays of orange-red coloration. The blossoms are tangerine red on the upper surface and geranium red on the under surface and exhibit a long vase life. The plant exhibits a strong and vigorous growth habit and is well suited for the production of cut flowers in a greenhouse.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) of the new variety was an unintroduced variety produced by a number of crosses. Initially the product of the cross of the Meihand 135F variety and the Meikim 00175F variety was crossed product of the cross of the Alain variety and the Orange Triumph variety. The resulting plant was then crossed with the Delpo 00235F variety to form the female parent. The male parent (i.e., the pollen parent) of the new variety was the Korrigan variety. The parentage of the new variety can be summaried as follows:

{[(*MEIHAND* 135F × *MEIKIM* 00175F) ×

(*ALAIN* × *ORANGE TRIUMPH*)] × *DELPO* 00235F} ×

*KORRIGAN.*

The seeds resulting from the above pollination were sown in a greenhouse and 556 plantlets were obtained which were physically and biologically different from each other. Selective study resulted in the identification of a single plant of the new variety.

The new variety meets well the needs of the greenhouse floricultural industry by providing a novel and highly attractive product which readily can be marketed in the form of cut flowers.

It was found that the new variety of Floribunda rose plant of the present invention possesses the following combination of characteristics:

(a) forms attractive long lasting multiple blossom floral sprays wherein the blossoms are tangerine red on the upper surface and geranium red on the under surface,
(b) is particularly well suited for growing under greenhouse conditions, and
(c) exhibits a strong and vigorous growth habit.

The new variety has been found to undergo asexual propagation by a number of routes, including budding, winter bench grafting, etc. The characteristics of the new variety have been found to be strictly transmissible by such asexual propagation from one generation to another.

The new variety has been named the Meirospray variety.

BRIEF DESCRIPTION OF THE PHOTOGRAPH

The accompanying photograph shows as nearly true as it is reasonably possible to make the same, in a collor illustration of this character, typical specimens of the plant parts of the new variety. The rose plants of the new variety were observed during September while grafted on *Rosa indica* understock and growing in a greenhouse at Cap d'Antibes, France.

DETAILED DESCRIPTION

Figures 1, 2, 3, 4, 5, 6, 7, 8, 9, 10, 11, 12, 13, 14, 15, 16:
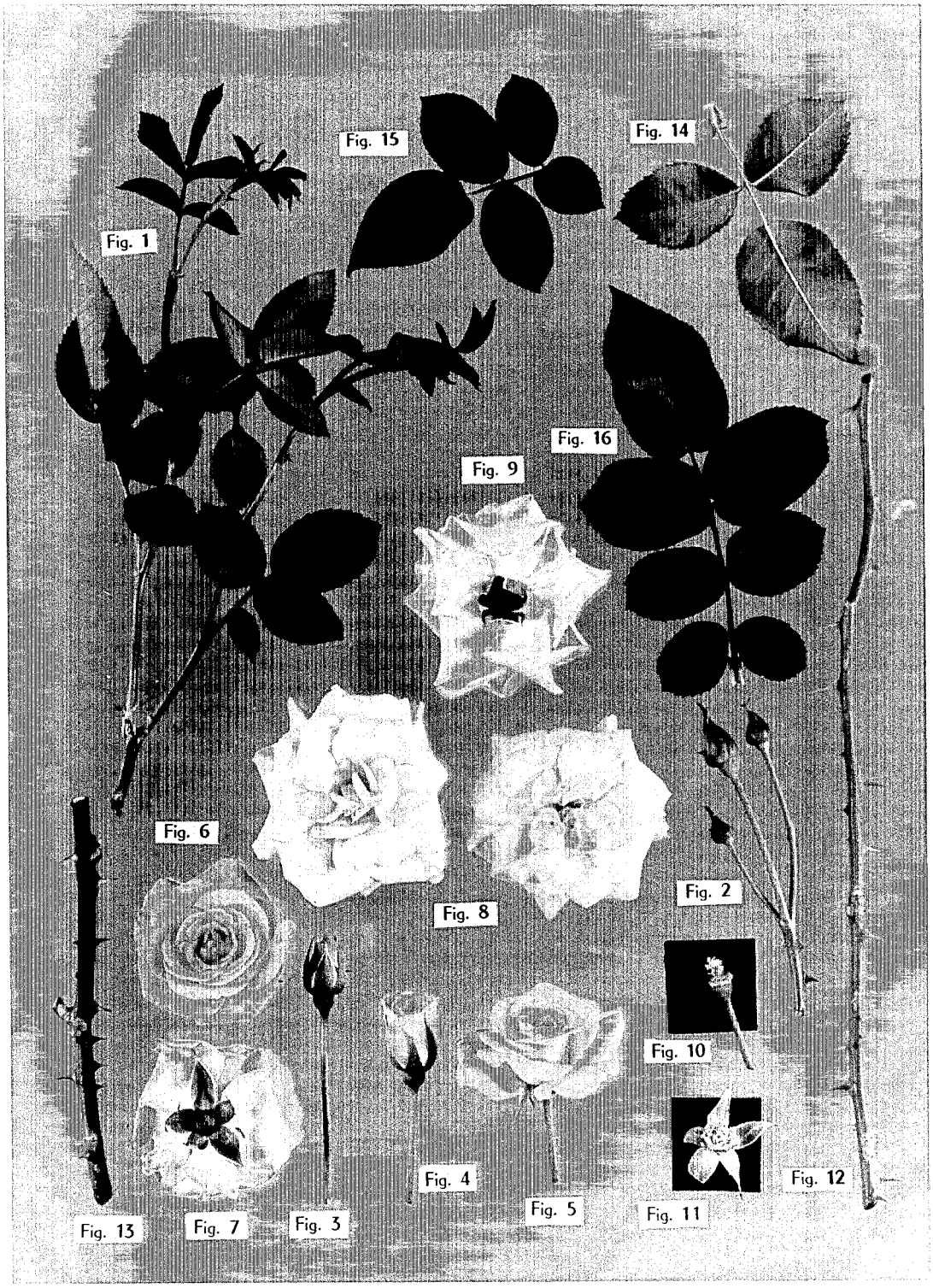
FIG. 1 illustrates a specimen of a young shoot.
FIG. 2 illustrates specimens of three floral buds before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower—plan view—obverse.
FIG. 7 illustrates a specimen of a fully open flower—plan view—reverse.
FIG. 8 illustrates specimens of fully open flowers prior to petal drop—plan view—obverse.
FIG. 9 illustrates a specimen of a fully open flower immediately prior to petal drop—plan view—reverse.
FIG. 10 illustrates a specimen of a floral receptacle showing the arrangement of the pistils (stamens removed)
FIG. 11 illustrates a specimen of a floral receptacle showing the arrangement of the stamens and pistils.
FIG. 12 illustrates a specimen of a flowering stem.
FIG. 13 illustrates a specimen of a main branch.
FIG. 14 illustrates a specimen of a leaf with three leaflets—under surface.
FIG. 15 illustrates a specimen of leaf with five leaflets—upper surface.
FIG. 16 illustrates a specimen of a leaf with seven leaflets—upper surface.

The chart used in the identification of the colors is that of The Royal Horticultural Society (R.H.S. Colour Chart). The description is based on one year old specimens of the new variety during September while grafted on *Rosa indica* understock and growing in a greenhouse at Cap d'Antibes, France.

Class: Floribunda.

Plant:

*Height.*—Plants which were pruned to a height of 85 cm. produced floral stems having a length of approximately 25 to 60 cm.

*Habit.*—Upright.

Branches:

*Color.*—Young stems: light green, Yellow-Green Group 144B. Adult wood: medium green, Yellow-Green, Group 146B.

Leaves:

*Petioles.*—Upper surface: noticeable veination, reddish brown on young foliage and medium green sometimes with a reddish tinge on adult foliage. Under surface: light green, sometimes with several small thorns.

*Leaflets.*—Number: 3, 5, and 7 (most often). Shape: elliptic lancelate. Serration: simple and regular. General appearance: ample, dense, and somewhat dull. Color (young foliage): upper surface: light green, Yellow-Green Group 146B, with large areas of reddish brown shading. under surface: reddish brown. Color (adult foliage): upper surface: Yellow-Green Group 146A. under surface; Yellow-Green Group 147B sometimes with reddish shading.

Inflorescence:

*Number of flowers.*—Commonly multiple per stem which opens substantially uniformly and substantially simultaneously.

*Peduncle.*—Its length is approximately 5.5 cm. on average.

*Buds.*—Shape: oval. Length: approxiomately 1.5 cm. on average. Color upon opening: upper surface: Red Group 43B. under surface: carmine red, Red Group 52A.

*Flower.*—Diameter: approximately 6 cm. on average. Color (when opening begins): upper surface: tangarine red, Red Group 40C. under surface: geranium red, Red Group 43C and Red Group 43D towards center. Color (when partially open): upper surface: tangerine red, Red Group 40C. under surface: geranium red, Red Group 43C and Red Group 43D towards the center. Color (at end of opening): upper surface: Red Group 42C on petal margins and Red Group 42D towards the center. under surface: geranium red, Red Group 43C and Red Group 43D towards the center. Fragrance: slight. Lasting quality: long. Petal number: approximately 25 to 30 on average.

Petal form: usually round and slightly pointed at the central tip of the petal. Stamen number: approximately 108 on average. Anthers: ochre and lightly tinged with fuschia at the center.

I claim:

1. A new and distinct variety of Floribunda rose plant characterized by the following combination of characteristics:

(a) forms attractive long lasting multiple blossom floral sprays wherein the blossoms are tangerine red on the upper surface and geranium red on the under surface, (b) is particularly well suited for growing under greenhouse conditions, and (c) exhibits a strong and vigorous growth habit; substantially as herein shown and described.

* * * * *